United States Patent [19]

Crooks

[11] Patent Number: 5,169,846
[45] Date of Patent: Dec. 8, 1992

[54] NON-AQUEOUS MICELLAR SOLUTIONS OF ANTHELMINTIC BENZIMIDAZOLES, CLOSANTEL, OR PHENOTHIAZINE, AND INSECT GROWTH REGULATORS

[76] Inventor: Michael J. Crooks, 29 Colwell Crescent, Chatswood NSW 2067, Australia

[21] Appl. No.: 595,906

[22] Filed: Oct. 11, 1990

[30] Foreign Application Priority Data

Oct. 12, 1989 [AU] Australia ............... PJ6807

[51] Int. Cl.⁵ ............ A01N 43/84; A01N 43/52; A01N 47/30; A01N 37/18
[52] U.S. Cl. ............... 514/224.8; 514/395; 514/594; 514/617
[58] Field of Search ............ 514/395, 224.8, 617, 514/594

[56] References Cited

U.S. PATENT DOCUMENTS 5,036,069 7/1991 Andrews et al. ............... 514/249

Primary Examiner—Richard L. Raymond
Assistant Examiner—S. Mark Clardy
Attorney, Agent, or Firm—Cohen, Pontani, Lieberman, Pavane

[57] ABSTRACT

A non-aqueous micellar solution, for use in animal health, of one or more non water-soluble Anthelmintics and or insect growth regulators in a polyethoxylated oil or fat surfactant and one or more co-solvents chosen from a group comprising dimethyl sulphoxide (DMSO), N-methyl pyrollidone (NMP), tetraglycol (TG) and propylene glycol (PG).

19 Claims, No Drawings

NON-AQUEOUS MICELLAR SOLUTIONS OF ANTHELMINTIC BENZIMIDAZOLES, CLOSANTEL, OR PHENOTHIAZINE, AND INSECT GROWTH REGULATORS

The present invention relates to non-aqueous micellar solutions of anthelmintics and insect growth regulators used to enhance animal health and to a method for preparation of such solutions.

Many anthelmintics such as the Benzimidazole carbamates (BZs) Phenothiazine or Closantel and Insect Growth Regulators (IGR's) such as Diflubenzuron are highly water-insoluble compounds with a water solubility typically less than 1 ppm. The literature states that BZ's are only soluble in concentrated acids and IGR's are only soluble in toxic solvents such as dimethylformamide or dioxane. Closantel is only soluble in concentrated alkali.

Because of the low solubility of these compounds they are generally administered in animal health in the form of suspensions; that is a physical dispersion of fine particles of the compound (usually 10–50 um) in an aqueous base (in the case of BZ's) or an aqueous or oily base (in the case of IGR's). Up until now the route of administration of the BZ's has been oral in sheep, horses, goats, cats and dogs and oral or intraruminal injection in cattle. In all cases the absorbtion of the BZ's is poor, it may be as low as 10% in monogastric species, and only up to 50% in ruminants where the rumen aids in the absorbtion process. The achievement of peak plasma levels however is slow and variable from animal to animal. Anthelmintic activity is related to plasma concentration of the BZ and thus the higher the plasma level peak the greater the activity. In practice oral suspensions are given at a much higher dosage than is necessary to achieve reasonable plasma levels and the majority of the dose is excreted in the faeces unabsorbed. In the case of some BZ's such as fenbendazole and albendazole, some of the metabolites have anthelmintic activity. A metabolite of fenbendazole is oxfendazole which is sold commercially. In the case of mebendazole only the parent compound has anthelmintic activity.

In monogastric species such as the dog the BZ's are the drug of choice for some worms such as hydatids but the absorbtion is so poor that dosage with an oral suspension has to be given over a five day period to achieve reasonable blood levels.

Insect growth regulators such as Diflubenzuron are being used experimentally as a spray on cattle and sheep with the aim that a residual of drug will be deposited in the animal and inhibit the maturation of insect parasites such as blowfly, lice and ticks. To achieve this the drug must be absorbed across the skin and achieve skin and plasma levels. The current formulations are suspensions generally in an aqueous or oil base often with a carrier substance such as kaolin. The IGR is poorly absorbed from these products.

It is an object of the present invention to overcome one or more of the abovementioned disadvantages associated with existing non-water soluble Anthelmintics and Insect Growth Regulators when such products are applied to animals or at least to provide the market with a choice.

The present invention discloses a non-aqueous micellar solution of one or more non-water soluble Anthelmintics and/or Insect Growth Regulators in polyethoxylated castor oil and one or more co-solvents chosen from a group comprising Dimethyl Sulphoxide (DMSO), N-Methyl Pyrollidone (NMP), Tetraglycol (TG) and Propylene Glycol (PG).

The present invention additionally discloses a method of preparing a stable non-aqueous micellar solution containing one or more active ingredients in the nature of a non-water soluble Anthelmintics or non-water soluble Insect Growth Regulators comprised of the steps of a) dissolving or dispersing the active or actives in an anhydrous solvent or solvents chosen from the group comprising Dimethyl Sulphoxide, N-Methyl Pyrolidone, Tetraglycol and Propylene glycol;

b) adding a surfactant in the nature of Polyethoxylated Castor Oil or another polyethoxylated fat to the resulting mixture;

c) stirring the resulting mixture whilst using ultrasonics and/or elevated temperature in order to disperse the active in the solvent/surfactant mixture whilst ensuring that the temperature does not exceed that at which the stability of the active may be compromised;

d) continuing to stir the resulting mixture until a clear product results.

The advantages of the present invention are well illustrated by the following discussion and example using carbamates and in particular Benzimidazole carbamates as an example of broad-spectrum anthelmintic drugs. By inhibiting tubulin polymerization and depending on the selective affinity and toxicity of carbamates towards different tubulins, carbamates can have anthelmintic, antifungal or even anticancer activity. Without limiting the scope of the present invention, further discussion will illustrate their anthelmintic activity.

Their almost insoluble nature in water, typically less than 0.01% W/v presents the major problem in their use. Consequently their absorption in humans and animals is very poor and highly variable.

In order to achieve the desired anthelmintic effect, large dosages of the compounds are used resulting in a high cost of treatment. As an example the bio-availability of Mebendazole ranges from as low as 1% in dogs to 33% in pigs.

Known formulations of the compounds are in tablets, aqueous suspension, oil dispersion or suppositories.

It is known to increase the solubility of poorly water-soluble drugs by dissolving them in micelles of an aquous solution of surfactant. However, there is a limit to the increase in solubility achievable by this method, dependant on the water-solubility of the drug, on the capacity of the micelles and on the desired consistency of the end product.

Carbamates, when administered in suspension, are absorbed with fat in the gastrointestinal tract into lymph giving a low blood level prolonged over a sustained period. In addition the method of administration of an almost water-insoluble drug itself presents problems in different species. As an example, it is difficult to drench cattle and thus the normal form of administration of a drug is by injection into the rumen. This can be difficult to administer and causes trauma to the animal.

Carbamates and in particular Benzimidazole carbamates are used and can be used in large dosage form because of their almost inert nature, i.e. they have low incidence of side effects giving high safety margins in dosage.

It is obvious that not withstanding the high safety margins a lower but effective dosage is always preferred.

It has surprisingly been discovered that poorly-water-soluble drugs can have their bio-availability increased by dispersion of the drug in a non-aqueous mixture of a surfactant and a co-solvent with heating. The resultant product is free-flowing and completely miscible with water. A concentration of 5% drug compound is easily achieved and with some drugs an even higher concentration is possible.

In this more water-soluble form the drug can be absorbed by passive diffusion in the liver. This achieves higher liver levels and consequently higher blood levels. There is potential for increased drug activity at lower dosage rates against for example liver flukes and hydatid cysts.

In addition this more water-soluble form of the drug could allow transport of the drug across the skin and so permit administration in a pour-on formulation. Pour-on formulations are useful in treating parasites in cattle. The fact that drugs prepared in accordance with the present invention give a clear and water-soluble solution facilitates administration of the drugs by intra-muscular and/or subcutaneous injection at a diversity of sites on an animal.

The following example illustrates the present invention.

EXAMPLE

Albendazole (5 g) in fine powder form is dispersed with vigorous stirring in 10 g of DMSO (co-solvent). 85 g of polyethoxylated castor oil (surfactant) is added and the mixture heated with stirring until a clear product results. The resulting product is allowed to air cool.

Anthelmintics and Insect Growth Regulators may be applied to animals in the nature of dogs, sheep, cattle etc. either topically, orally or by subcutaneous or intramuscular injection. Depending upon the active being utilised and the method of application which is preferred different solvents or combinations of solvents may be utilised from the group comprising Dimethyl Sulphoxide, N-Methyl Pyrollidone, Tetraglycol and Propylene Glycol. The surfactant Polyethoxylated Castor Oil has been found to be most appropriate. It is desirable in order that the resulting product be of the desired viscosity that the ratio of ethylene oxide to castor oil in the surfactant be between 20:1 and 60:1.

The solvent dimethyl sulphoxide is principally only of interest in relation to actives which are to be applied topically whereas N-Methyl Pyrollidone is usually the principal co-solvent utilised where the active is to be applied orally or by injection. With injectable products it is conventional wisdom to use multiple solvent systems to minimise the possibility of unwanted side-reactions or side-effects in the animal which could result from the use of single solvents due to the greater concentration of such solvent when used alone rather than in combination with other solvents. The ratio of surfactant to solvent is largely determined by the affinity of the particular active involved for the micelles in the solution and for example where a topical solution of Mebenzadole is being prepared using DMSO solvent and Polyethoxylated Castor Oil the ratios of Polyethoxylated Castor Oil to co-solvent to active are 17/2/1 whereas where active ingredients such as Diflubenzuron is being utilised whether for oral injection or topical use the optimal ratio of Polyethoxylated Castor Oil Surfactant to co-solvent to active is approximately 10/30/1.

Table 1A hereafter sets out a number of actives along with appropriate proportions of co-solvent/s and surfactant for various applications.

TABLE IA

OPTIMAL RATIOS OF ACTIVE TO CO-SOLVENT AND POLYETHOXYLATED CASTOR OIL AND HEATING TEMPERATURES REQUIRED

| ACTIVE | ROUTE (O = oral) (T = topical) (I = injectable) | OPTIMAL RATIO OF ACTIVE TO TOTAL MIXTURE BY WEIGHT | (Possible range of Active Content by weight) | OPTIMAL RATIO OF CO-SOLVENT(S) TO TOTAL MIXTURE BY WEIGHT |
|---|---|---|---|---|
| LUXABENDAZOLE | O/T/I | 1 | (0–10%) | NMP 20, TG 10, & PG 10 |
| MEBENDAZOLE/ ALBENDAZOLE/ FENBENDAZOLE/ OXFENDAZOLE | T | 1 | (0–5%) | DMSO 2 |
| MEBENDAZOLE/ ALBENDAZOLE/ FENBENDAZOLE/ OXFENDAZOLE | O/T/I | 1 | (0–5%) | NMP 15 & TG 15, |
| FLUBENDAZOLE | O/T/I | 1 | (0–5%) | NMP 20, TG 10, & PG 10 |
| CLOSANTEL | O/T/I | 1 | (0–8%) | NMP 10 |
| PHENOTHIAZINE | O/I | 1 | (0–10%) | NMP 8 |
| DIFLUBENZURON | O/T/I | 1 | (0–5%) | NMP 20, TG 10 & PG 10 |

| ACTIVE | ROUTE (O = oral) (T = topical) (I = injectable) | OPTIMAL RATIO OF POLY-ETHOXYLATED CASTER OIL TO TOTAL MIXTURE BY WEIGHT | (Possible range by weight) | HEATING TEMP. |
|---|---|---|---|---|
| LUXABENDAZOLE | O/T/I | 10 | (10–40%) | Room T. |
| MEBENDAZOLE/ ALBENDAZOLE/ FENBENDAZOLE/ OXFENDAZOLE | T | 17 | (40–85%) | 90° |
| MEBENDAZOLE/ ALBENDAZOLE/ FENBENDAZOLE/ OXFENDAZOLE | O/T/I | 20 | (20–50%) | 50° |

TABLE IA-continued

OPTIMAL RATIOS OF ACTIVE TO CO-SOLVENT AND POLYETHOXYLATED CASTOR OIL AND HEATING TEMPERATURES REQUIRED

| | | | | |
|---|---|---|---|---|
| FLUBENDAZOLE | O/T/I | 10 | (10-50%) | 25° |
| CLOSANTEL | O/T/I | 15 | (20-70%) | Room T. |
| PHENOTHIAZINE | O/I | 12 | (20-70%) | Room T. |
| DIFLUBENZURON | O/T/I | 10 | (10-70%) | Room T. |

In all instances however the bio-availability of the active ingredient is greatly enhanced by incorporation of same into the non-aqueous micellar solution as will be observed from the test results set out hereafter.

TEST RESULTS

In order to compare the effectiveness of a micellar preparation in accordance with the present invention containing the active anthelmintic ingredient Mebendazole the presently available commercial formulation utilising the same active ingredient called "Telmin" TM an experiment was devised involving sheep and the monitoring of faecal egg count depression following treatment. The Mebendazole formulation in accordance with the present invention will hereinafter be referred to as "Nutrex".

The experiment was performed in accordance with the following parameters:

32 young lambs of mixed sex and varying between 2-8 months of age were infected with 1900 L3, of a BZ susceptible strain of Haemonchus contortus. Infection was by intraruminal injection.

Faecal egg counts were carried out 28 days after infection, following which sheep were allotted to groups using a method of restricted randomisation, based on the faecal egg counts.

Treatments were then carried out at 0.85, 1.0625 and 1.328 mg/kg of mebendazole as Telmin and 0.55, 0.6875 and 0.86 mg/kg of mebendazole as Nutrex. The dose rate was developed from an earlier experiment in which an estimate of the lowest limit of activity was sought. All treatments were adminstered by intra-ruminal injection.

Seven days after treatment facecal egg counts were carried out and the group mean total egg counts compared. An untreated control group was included to allow adjustment of the egg counts in treated animals.

RESULTS

Results of treatment are set out in Table 1 which shows that the efficacy range of Telmin was from 3-90% and for Nutrex 50-86%.

In order to compare the formulations more precisely all faecal egg counts were subjected to logarithmic transformation and the efficacy of treatment calculated. The procedure also facilitated the calculation of the dose rate required for 25, 50, 75 and 100% efficacy (using linear regression analysis). The values obtained from transformed data are set out in Table II. The calculated values are included in Table III.

TABLE I

Faecal Egg Counts (eggs/g of faeces) before and after Treatment

| Grp/No. | Pre | Post | Adj. Cnts |
|---|---|---|---|
| 1-2 | 8350 | 14400 | 12643 |
| 5 | 12250 | 11150 | 9790 |
| 18 | 7000 | 4600 | 4039 |
| 19 | 2400 | 2950 | 2590 |
| avg | 7500 ± 4063 | 8275 ± 5405 | 7266 |

TABLE I-continued

Faecal Egg Counts (eggs/g of faeces) before and after Treatment

| Grp/No. | Pre | Post | Adj. Cnts |
|---|---|---|---|
| % efficacy 1.8 | | | |
| 3-6 | 8250 | 8400 | 5619 |
| 7 | 12200 | 4250 | 3732 |
| 9 | 5500 | 3950 | 3468 |
| 29 | 2050 | 1150 | 1010 |
| avg | 7000 ± 4296 | 3938 ± 2154 | 3457 |
| % efficacy 49.9 | | | |
| 5-10 | 15300 | 200 | 176 |
| 15 | 12000 | 6000 | 527 |
| 30 | 1850 | 2000 | 1758 |
| 31 | 4300 | 950 | 834 |
| avg | 8363 ± 6332 | 938 ± 771 | 823 |
| % efficacy 90.0 | | | |
| 7-8 | 8550 | 5950 | — |
| 14 | 3700 | 3300 | — |
| 16 | 13000 | 16600 | — |
| 17 | 7500 | 10900 | — |
| avg | 8188 ± 3825 | 9188 ± 5860 | — |
| % increase 12.2 | | | |
| 2.1 | 2050 | 4000 | 3512 |
| 12 | 12250 | 1750 | 1537 |
| 21 | 8350 | 3250 | 2854 |
| 22 | 5800 | 4200 | 3688 |
| avg | 7113 ± 4293 | 3300 ± 1111 | 2898 |
| % efficacy 58.7 | | | |
| 4.4 | 8000 | 2850 | 2502 |
| 13 | 20000 | 4450 | 3907 |
| 28 | 4500 | 1000 | 878 |
| 32 | 2000 | 600 | 527 |
| avg | 8625 ± 7973 | 2225 ± 1778 | 1954 |
| % efficacy 77.0 | | | |
| 6.3 | 14450 | 2350 | 2063 |
| 11 | 10400 | 1350 | 1185 |
| 20 | 1000 | 1450 | 1273 |
| 24 | 7550 | 300 | 263 |
| avg | 8350 ± 5659 | 1363 ± 839 | 1198 |
| % efficacy 85.5 | | | |

TABLE 2

EFFICACY ANALYSIS
Log transform all data and Estimate Efficacy

| Group | Gx̄Pre | Gx̄Post | % Efficacy |
|---|---|---|---|
| 1 | 6439 | 5999 | 6.75 |
| 2. | 5905 | 2745 | 53.5 |
| 3 | 5804 | 2928 | 49.6 |
| 4 | 6160 | 1458 | 76.3 |
| 5. | 6182 | 607 | 90.2 |
| 6 | 5804 | 951 | 83.6 |

SUMMARY

| Telmin | % Efficacy | Nutrex | % Efficacy |
|---|---|---|---|
| 0.85 mg/kg | 6.8 | 0.55 mg/kg | 53.5 |
| 1.0625 mg/kg | 49.6 | 0.6875 mg/kg | 76.3 |
| 1.328 mg/kg | 90.2 | 0.88 mg/kg | 83.6 |

TABLE III

Data from Dose/Response Regression Analysis

| Calculated Efficacy (%) | Dose Rate (mg/kg) | | N/T % |
|---|---|---|---|
| | Telmin | Nutrex | |
| 25 | 0.8 | 0.1 | 12.5 |
| 50 | 1.17 | 0.46 | 39.3 |
| 75 | 1.25 | 0.75 | 60.0 |

TABLE III-continued

| Data from Dose/Response Regression Analysis | | | |
|---|---|---|---|
| Calculated | Dose Rate (mg/kg) | | |
| Efficacy (%) | Telmin | Nutrex | N/T % |
| 100 | 1.30 | 0.95 | 73.0 |

INTERPRETATION OF RESULTS

Using the regression equations
Y (Log. % efficacy)= −0.99+2.2999 X (dose rate) for Telmin and
Y (Log. % efficacy)=1.4197+0.6075 X (dose rate) for Nutrex the dose rates required to achieve efficacies of 25%, 50%, 75% and 100% were calculated and are set out in table III. It can be seen that at the lowest efficacy value Nutrex achieves the result with only 12.5% of the amount of mebendazole delivered by the Telmin formulation, but that at 100% efficacy the value has risen to 73% of that of Telmin.

Various Anthelmintics and insect growth regulators have been formulated in accordance with the methods and co-solvents described in this invention and a table of such actives giving the preferred method of administration as well as the approximate proportions of active, co-solvent and Polyethoxylated Castor Oil as well as the appropriate heating temperature is set out in Table IA hereof as aforementioned.

It will be appreciated from Table IA that each active listed in column 1 has a different affinity for the micelles created in the solvent/surfactant mix and consequently differing proportions of actives may be contained in the resulting mixture. The choice of solvent is to some extent dictated by the intended route of administration of the mixture (i.e. either oral, topical or injectable). For example it can be seen that DMSO is only appropriate where topical administration is required whereas other solvents or mixtures of solvents are appropriate for either injectable, topical or indeed all three types of application. It will be noted that the table gives an optimal ratio of active to solvent to Polyethoxylated Castor Oil for each active based upon weight as well as a range of feasible percentages which could be achieved in respect of the active and the surfactant (again by weight) depending upon the concentration of active which would be required in any particular application. The percentage of the final mixture which is comprised by surfactant may well be dictated by the required percentage of active as if a relatively high concentration of active is required then a relatively high proportion of surfactant will be required in order that the micelles can accommodate the active.

It will be noted that a number of the actives can be incorporated into a clear micellised solution at room temperature whereas others require elevated temperature. As an alternative to elevating the temperature agitation by ultrasonic means can be utilised in order to disperse the active in the solvent/surfactant mixture. In practice it is often not necessary to resort to ultrasonic agitation as the temperatures required in most instances are not excessive.

In cases where ultrasonic agitation is utilised a small elevation in temperature is also desirable but naturally the temperature must be kept below that which would result in any degredation of the active being incorporated into the mixture.

It is envisaged that other surfactants apart from Polyethoxylated Castor Oil may be utilised as a surfactant in accordance with the method disclosed in this invention and for example sorbitan esters such as Tweens and Crills could be utilised or indeed other polyethoxylated fats.

The claims defining the invention are as follows:

1. A clear, water miscible non-aqueous micellar solution comprising an anthelmintically effective amount of one or more non-water soluble Anthelmintics selected from the group consisting of Luxabendazole, Mebendazole, Albendozole, Fenbendazole, Oxfendazole, Flubendazole, Closantel and Phenothiazine and/or an insect growth regulator; a polyethoxylated oil or fat surfactant; and one or more co-solvents chosen from a group comprising Dimethyl Sulphoxide (DMSO), N-Methyl Pyrollidone (NMP), Tetraglycol (TG) and Propylene Glycol (PG).

2. A method of preparing a stable clear, water miscible non-aqueous solution containing one or more actives in the nature of a non-watersoluble Anthelmintics or non-watersoluble insect growth regulators comprised of the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of Polyethoxylated Castor Oil or another polyethoxylated fat to the resulting mixture;
   c) stirring the resulting mixture whilst using ultrasonics and/or elevated temperature in order to disperse the active or actives in the solvent/surfactant mixture whilst ensuring that the temperature does not exceed that at which the stability of the active may be comprised;
   d) continuing to stir the resulting mixture until a clear product results.

3. A non-aqueous micellar solution containing Luxabendazole for adminstration to animals either orally, topically or by injection containing between 1–10% Luxabendazole by weight, between 10–40% by weight Polyethoxylated Castor Oil as surfactant; the balance of the mixture substantially comprising a solvent formed from one or more of the solvents N-Methyl Pyrollidone, Tetraglycol and Propylene Glycol.

4. A non-aqueous micellar solution containing Mebendazole, Albendazole, Fenbendazole or Oxfendazole for topical administration to animals containing between 0–5% Mebendazole, Albendazole, Fenbendazole or Oxfendazole by weight, between 40–85% by weight Polyethoxylated Castor Oil as surfactant the balance of the mixture substantially comprising the solvent DMSO.

5. A non-aqueous micellar solution containing Mebendazole, Albendazole, Fenbendazole or Oxfendazole according to claim 4 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Cator Oil or another polyethoxylated fat to the resulting mixture;
   c) stirring the resulting mixture whilst using ultrasonics and/or elevated temperature in order to disperse the active or actives in the solvent/surfactant mixture while insuring that the temperature does not exceed that at which the stability of the active may be compromised;
d) continuing to stir the resulting mixture until a clear product results.

6. A non-aqeous micellar solution containing Mebendazole, Albendazole, Fenbendazole or Oxfendazole according to claim 4 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Castor Oil or another polyethoxylated fat to the resulting mixture;
   c) stirrig the resulting mixture whilst using ultrasonics and/or elevated temperature in order to disperse the active or actives in the solvent/surfactant mixture while insuring that the temperature does not exceed that at which the stability of the active may be compromised;
   d) continuing to stir the resulting mixture until a clear product results; and wherein the heat of the mixture during the stirring step is between 80 and 95 degrees Celsius.

7. A non-aqeous micellar solution containing Mebendazole, Albendazole, Fenbendazole or Oxfendazole for administration to animals either orally, topically or by injection containing between 1-5% Mebendazole, Albendazole, Fenbendazole or Oxfendazole by weight, between 20-50% by weight Polyethoxylated Castor Oil as surfactant; the balance of the mixture substantially comprising a solvent formed from one or more of the solvents N-Methyl Pyrollidone and Tetraglycol.

8. A non-aqueous micellar solution containing Mebendazole, Albendazole, Fenbendazole or Oxfendazole according to claim 7 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol:
   b) adding a surfactant in the nature of a Polyethoxylated Castor Oil or another polyethoxylated fat to the resulting mixture:
   c) stirring the resulting mixture whilst using ultrasonic and/or elevated temperature in order to disperse the actives in the solvent/surfactant mixture while insuring that the temperature does not exceed that at which the stability of the active may be compromised:
   d) continuing to stir the resulting mixture until a clear product resluts.

9. A non-aqueous miceller solution containing Mebendazole, Albendazole, Fenbendazole or Oxfendazole according to claim 7 when prepared by the steps of:
   a) dissolving or dispersing an active or actives in an anhydrous solvent or solvents chosen from the group comprising Dimethyl Sulphoxide, N-Methyl Pyrollidone, Tetraglycol and Propylene Glycol;
   b) adding a surfactant in the the nature of Polyethoxylated Castor Oil or another polyethoxylated fat to the resluting mixture;
   c) stirring the resulting mixture while using ultrasonics and/or elevated temperature in order to disperse the active or actives in the solvent/surfactant mixture while ensuring that the temperature does not exceed that at which the stability of the active may be comprised;
   d) continuing to stir the resulting mixture until a clear product results;
and wherein the heat which is supplied during the stirring step is between 45 and 55 degrees Celsius.

10. A non-aqueous miceller solution of one or more non-water soluble Anthelmics and/or insect growth regulators in accordance with claim 9, wherein the surfactant is not Polyethoxylated Castor Oil but another suitable polyethoxylated fat or sorbitan ester such as Tweens or Crills.

11. A non-aqueous miceller solution containing Flubendazole for administration to animals either orally, topically or by injection containing between 1-5% Flubendazole by weight, between 10-50% by weight Polyethoxylated Castor Oil as surfactant; the balance of the mixture substantially comprising a solvent formed from one or more of the solvents N-Methyl Pyrollidone, Tetraglycol and Propylene Gylcol.

12. A non-aqueous micellar sollution containing Flubendazole according to claim 11 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol:
   b) adding a surfactant in the nature of a Polyethoxylated Casor Oil or another polyethoxylated fat to the resulting mixture:
   c) stirring the resulting mixture whilst using ultrasonics and/or elevated temperature in order to disperse the active or actives in the solvent/surfactant mixture while insuring that the temperature does not exceed that at which the stability of the active may be compromised:
   d) continuing to stir the resulting mixture until a clear product results.

13. A non-aqueous miceller solution containing Closantel for administration to animals either orally, topically or by injection containing between 1-8% Closantel by weight, between 10-70% by weight Polyethoxylated Castor Oil as surfactant; the balance of the mixture substantially comprising the solvent N-Methyl Pyrollidone.

14. A non-aqueous micellar solution containing Closantel according to claim 13 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Castor Oil or another Polyethoxylated fat to the resulting mixture;
   c) stirring the resulting mixture whilst using ultrasonic and/or elevated temperature in order to disperse the active or actives in the solvent/surfactant mixture while insuring that the temperature does not exceed that at which the stability of the active may be compromised:
   d) continuing to stir the resulting mixture until a clear product results.

15. A non-aqueous miceller solution containing Phenothiazine for administration to animals either orally or by injection containing between 1-10% Phenothiazine by weight, between 20-70% by weight Polyethoxylated Castor Oil as surfactant; the balance of the mixture substantially comprising the solvent N-Methyl Pyrollidone.

16. A non-aqueous micellar solution containing Phenothiazine according to claim 15 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Castor Oil or another polyethoxylated fat to the resulting mixture;
   c) stirring the resulting mixture whilst using ultrasonics and/or elevated temperature in order to disperse the active or actives in the solvent/surfactant mixture while insuring that the temperature does not exceed that at which the stability of the active may be compromised;
   d) continuing to stir the resulting mixture until a clear product results.

17. A non-aqueous micellar solution containing Diflubenzuron for administration to animals either orally, topically or by injection containing between 1–5% Diflubenzuron by weight, between 10–70% by weight Polyethoxylated Castor Oil as surfactant; the balance of the mixture substantially comprising a solvent formed from one or more of the solvents N-Methyl Pyrollidone, Tetraglycol and Propylene Glycol.

18. A non-aqueous micellar solution containing Diflubenzuron according to claim 17 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Castor Oil or another polyethoxylated fat to the resulting mixture;
   c) stirring the resulting mixture whilst using ultrasonics and/or elevated temperature in order to disperse the active or actives in the solvent/surfactant mixture while insuring that the temperature does not exceed that at which the stability of the active may be compromised;
   d) continuing to stir the resulting mixture until a clear product results.

19. A non-aqueous micellar solution containing Luxabendazole according to claim 3 when prepared by the steps of:
   a) dissolving or dispersing the active or actives in an anhydrous solvent or solvents chosen from the group comprising Dimethyl Sulphoxide, N-Methyl Pyrollidone, Tetraglycol and Propylene Glycol;
   b) adding a surfactant in the nature of a Polyethoxylated Castor Oil or another polyethoxylated fat to the resulting mixture;
   c) stirring the resulting mixture whilst using ultrasonics and/or elevated temperature in order to disperse the active or actives in the solvent/surfactant mixture while insuring that the temperature does not exceed that at which the stability of the active may be compromised;
   d) continuing to stir the resulting mixture until a clear product results.

* * * * *